United States Patent [19]

Stüber

[11] Patent Number: 5,204,240

[45] Date of Patent: * Apr. 20, 1993

[54] METHOD AND A KIT CONTAINING MEANS FOR THE KINETIC DETERMINATION OF FACTOR XIII

[75] Inventor: Werner Stüber, Lahntal, Fed. Rep. of Germany

[73] Assignee: Behringwerke Aktiengesellschaft, Marburg/Lahn, Fed. Rep. of Germany

[*] Notice: The portion of the term of this patent subsequent to Sep. 17, 2008 has been disclaimed.

[21] Appl. No.: 333,371

[22] Filed: Apr. 5, 1989

[30] Foreign Application Priority Data

Apr. 7, 1988 [DE] Fed. Rep. of Germany ....... 3811647

[51] Int. Cl.$^5$ ..................... C12Q 1/56; G01N 33/86; C07K 7/06
[52] U.S. Cl. ....................................... 435/13; 436/69; 530/328
[58] Field of Search ............................ 435/13; 436/69; 530/328

[56] References Cited

U.S. PATENT DOCUMENTS 5,049,506  9/1991  Stuber .................................. 436/69

FOREIGN PATENT DOCUMENTS 0121995 10/1984 European Pat. Off. .
61-185198 8/1986 Japan .

OTHER PUBLICATIONS

Fesus et al., "Synthetic Gutamine Poptides as Substrates for the Kinetic Determination of Blood Coagulation Factor XIII," Clin Chem 31, 2044–45 (1985).
Gorman et al., J. Biol. Chem. 259:9007–9010 (1984).
J. J. Gorman et al., J. Biol. Chem. 255, No. 2, 419–427 (1980).
J. J. Gorman and J. E. Folk, "Peptides: Structure and Function, Proceedings of the American Peptide Symposium, 9th Toronto" pp. 363–366 (1985) Editors Deber et al.
Muszbek et al., "Kinetic Determination of Blood Coagulation Factor XIII in Plasma," Clinical Chemistry, vol. 31, No. 1, pp. 35–40 (1985).
Miraglia et al., "Measurement of Blood Coagulation Factor XIIIa Formation in Plasma Containing Glycyl-L-prolyl-L-arginyl-L-Proline," Analytical Biochemistry 144, pp. 165–171 (1985).

Primary Examiner—Christine M. Nucker
Assistant Examiner—M. P. Woodward
Attorney, Agent, or Firm—Finnegan, Henderson, Farabow, Garrett & Dunner

[57] ABSTRACT

A method for the detection and for the determination of blood coagulation factor XIII in plasma, as well as a kit containing means which can be used in this method, are described.

Used in this method are a fibrin-aggregation inhibitor, thrombin, a glutamine-containing peptide as substrate for factor XIII, an amine and a system for detecting ammonia which is formed.

The kit containing means which can be used in this method contains a fibrin-aggregation inhibitor and a glutamine-containing peptide, where appropriate in addition to other components necessary for the method.

12 Claims, 1 Drawing Sheet

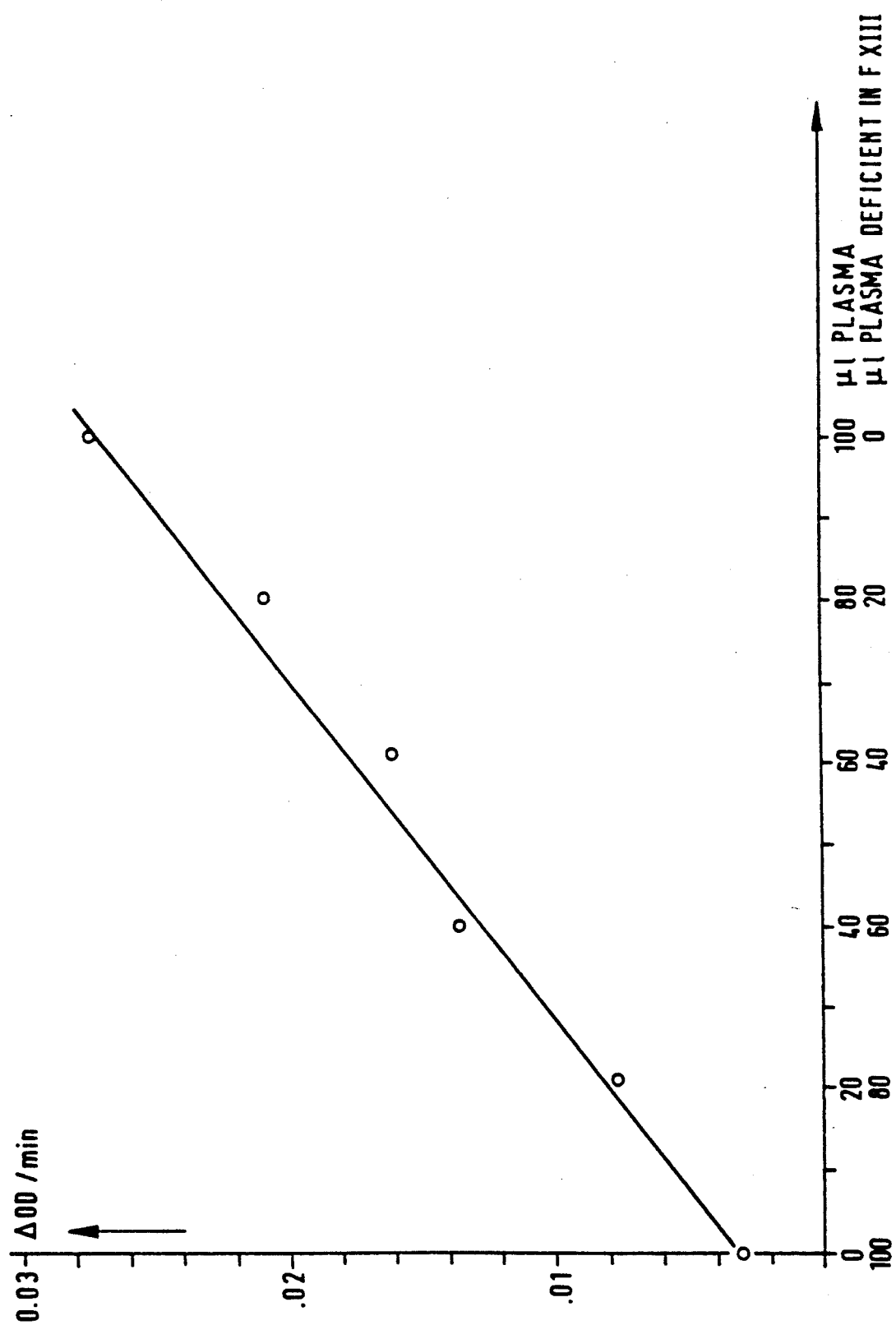

METHOD AND A KIT CONTAINING MEANS FOR THE KINETIC DETERMINATION OF FACTOR XIII

The invention relates to a method and a kit containing means for the qualitative and quantitative measurement of blood coagulation factor XIII.

Factor XIII is a transglutaminase which circulates in the plasma as a proenzyme and, when required, is activated by thrombin. In addition, platelets and placentae also exhibit factor XIII activity. The biochemical action of factor XIII comprises the cross-linking of fibrin monomers which are associated via hydrogen bonds, resulting in an insoluble fibrin clot. Besides the fibrin-stabilizing action, factor XIII has great importance in wound healing in that factor XIII increases the rate of development of the fibroblasts which are growing into the clot.

Because of the clinical relevance of factor XIII, the determination of this coagulation factor is of great importance. The following methods are essentially used for the quantitative measurement: incorporation of a radioactively labeled substrate into a protein, for example casein, determination of the solubility/insolubility of a clot; electroimmunodiffusion and the determination of the ammonia content during clot formation. The disadvantages associated with these detection methods is that they are time-consuming or are not straightforward to carry out.

Hence the object of this invention was to provide a method and a kit containing means for more straightforward and more rapid F XIII determination.

Analytical Biochemistry 144, 165-171 (1985) discloses the determination of F XIII in plasma, from which the fibrinogen has not been removed, with the addition of glycylprolylarginyl-proline, the substrate being "Hammersten" casein. The chosen detection method was the incorporation of $^3$H-putrescine.

Clinical Chemistry 31, 35-40 (1985) discloses the determination of the F XIII catalysed ammonia evolution using the substrate casein/ethylamine and the ammonia reagent NADH/GLDH/ketoglutarate.

We have found, surprisingly, that the determination of F XIII in plasma can be improved by using a glutamine-containing peptide as F XIII substrate in combination with a fibrin-polymerization inhibitor, and determining the F XIII via the ammonia which is formed, by means of a subsequent NADH-dependent reaction.

FIG. 1 shows the rate of change in the optical density (OD/time) as a function of the content of factor XIII in the sample. Different concentrations of F XIII in the samples were produced by mixing different defined amounts of a plasma and of a F XIII-deficient plasma.

Hence the invention relates to a method for the determination of factor XIII in F XIII-containing samples, for example in plasmas, in which the sample is activated with thrombin in the presence of a fibrin-aggregation inhibitor, for example Gly-Pro-Arg-Pro, and incubated with a substrate for factor XIII, with a primary amine and, where appropriate, with a buffer substance in solution, and the ammonia which is formed is determined using NADH, GLDH and ketoglutarate, wherein the substrate for F XIII is a glutamine-containing peptide.

Untreated samples, for example plasma, are directly pre-activated with a thrombin solution which is, where appropriate, prepared with a buffer solution, and the activated factor XIII which results from this is determined using a subsequent NADH-dependent measurement. The interfering effect of fibrinogen in the assay mixture is compensated by adding substances which prevent aggregation of fibrin monomers, for example Gly-Pro-Arg-Pro or Gly-Pro-Arg-Pro-Arg. Gly-Pro-Arg-Pro is preferably used as fibrin-aggregation inhibitor. Low molecular weight glutamine-containing peptides, selected from the sequences X-Cly-Pro-Gly-Gln-Ser-Lys-Val-Ile-Gly amide or X-Gly-Pro-Gly-Gln-Ser-Lys-Val-Leu-Gly amide, wherein X is a proton, a natural occuring amino acid or a corresponding D amino acid or a depeptide formed by these amino acids, preferably Leu-Leu-Gly-Pro-Gly-Gln-Ser-Lys-Val-Ile-Gly amide, Arg-Leu-Gly-Pro-Gly-Gln-Ser-Lys-Val-Ile-Gly amide, Gly-Pro-Gly-Gln-Ser-Lys-Val-Ile-Gly amide, most preferably Leu-Gly-Pro-Gly-Gln-Ser-Lys-Val-Ile-Gly amide, are used as substrate for F XIII. It is possible with this method to determine F XIII in a F XIII-containing solution reliably and rapidly. The assay procedure preferably contains the following steps:

the sample to be tested is placed in a vessel the fibrin-aggregation inhibitor, which is dissolved in a buffer solution where appropriate, is added thrombin is added, and the mixture is incubated for a period of 3-10 min., the ammonia evolution is measured, preferably by the system NADH, GLDH, ketoglutarate, amine and substrate.

This determination requires only a small sample volume. The F XIII measurement is preferably carried out in a 1 ml cuvette at 37° C., with a sample volume of 25 to 200 µl, particularly preferably 50 µl.

The F XIII is activated by addition of thrombin in the presence of the fibrin-aggregation inhibitor in a solution containing Ca ions. For this purpose, 2500 IU/l to 20,000 IU/l thrombin, preferably 7000 IU/l, are dissolved in a buffer which is preferably 10 mM to 75 mM in HEPES, preferably 30 mM and 75 mM to 200 mM in NaCl, preferably 100 mM. This buffer also has a Ca ion concentration of 20 mM to 200 mM, preferably 60 mM, and a thiol concentration, preferably dithiothreitol concentration, of 2.5 mM to 50 mM, preferably 17 mM. A fibrin-aggregation inhibitor, preferably Gly-Pro-Arg-Pro, has been added to this buffer in a concentration of 0.5 mM to 20 mM, preferably 1.5 mM and the pH has been adjusted with hydrochloric acid or sodium hydroxide solution to 7.0 to 8.2, preferably 7.6. 100 µl, preferably 150 µl, of this buffer are added to the sample, and the mixture is incubated for 3 to 10 minutes, preferably 5 minutes.

After the period of activation of factor XIII has elapsed, the detection reagents are added, preferably in the form of a prepared solution. In each case, the total solution in the cuvette is made up to 1 ml. The prepared solution of the detection reagents contains alpha-ketoglutarate, 1 mM to 20 mM, preferably 7 mM, plus NADH, 0.05 mM to 0.5 mM, preferably 0.125 mM, plus GLDH, 500 IU/l to 6000 IU/l, preferably 3000 IU/l, plus a substrate and an amine. Where appropriate, this solution also contains a buffer substance, preferably triethanolamine in a concentration of 20 to 200 mM, particularly preferably 100 mM.

The substrates used are the glutamine-containing peptides as described hereinbefore, the chosen final concentration of peptide in the above-mentioned assay mixture being in the range from 0.2 to 5 mg, preferably 1 mg, per ml of assay mixture.

Primary amines have proven beneficial as amines, these including substances such as ethanolamine, putrescine, cadaverine, diaminoethane and aminoethane, but preferably however glycine ethyl or methyl ester. These amines preferably taken up together with the substrate in the prepared solution of the detection reagents, the concentration of amine used being from 5 mM to 75 mM, but preferably 25 mM.

The pH of the detection reagent solution is adjusted to 7.2 to 8.5, preferably 8.0 with hydrochloric acid.

The change per unit time in the optical density at 340±15 nm which now occurs serves as a direct measure of the F XIII activity.

The invention also relates to a kit containing components for use in a method for the determination of F XIII, containing a fibrin-aggregation inhibitor and a glutaminecontaining peptide as substrate for F XIII, and, where appropriate, other reagents necessary for the method.

The examples which follow explain this in more detail:

EXAMPLE 1

Preparation of solution A

The following substances were dissolved in 100 mL of water: 793 mg of HEPES, 584 mg of sodium chloride, 882 mg of CaCl$_2$, 67 mg of Gly-Pro-Arg-Pro, 257 mg of dithiothreitol and 666 IU of thrombin. The pH was adjusted to 7.6 with sodium hydroxide.

Preparation of solution N

The following substances were dissolved in 100 ml of water: 10 mg of NADH, 155 mg of disodium alpha-ketoglutarate, 213 units of GLDH, 375 mg of glycine ethyl ester hydrochloride, 125 mg Leu-Gly-Pro-Gly-Gln-Ser-Lys-Val-Ile-Gly amide and 2.3 g of triethanolamine hydrochloride. The pH was adjusted to 8.0 with sodium hydroxide.

Assay procedure

50 μl of standard human plasma (1 unit of F XIII/ml) were pipetted into a 1 ml-capacity measuring cuvette (1 cm light path) and incubated with 150 μl of solution A at 37° C. After 5 minutes had elapsed, 800 μl of solution N were added, and the change in extinction at 334 nm was measured and recorded on a pen recorder. The measurement was continued for 5 minutes. The optical density showed a change of 0.015 per minute.

EXAMPLE 2

See example 1 for preparation of solutions A and N. 100 μl of F XIII-deficient plasma were incubated with 150 μl of solution A at 37° C. for 5 minutes. 750 μl of solution N were added and then the activity was measured at 334 nm. Subsequent to this 80 μl of F XIII-deficient plasma were measured with 20 μl of standard human plasma in the same way. So were the combinations 60 μl of deficient plasma/40 μl of standard plasma, 40 μl of deficient plasma/60 μl of standard plasma, 80 μl of standard plasma/ 20 μl of deficient plasma and 100 μl of standard plasma. The measured values are evident from the diagram (FIG. 1).

ABBREVIATIONS

NADH: nicotinamide adenine dinucleotide, reduced
GLDH: glutamic dehydrogenase
nm: nanometers
Gly: glycine
Pro: L-proline
Arg: L-arginine
Leu: L-leucine
Gln: L-glutamine
Ser: L-serine
Lys: L-lysine
Val: L-valine
Ile: L-isoleucine
HEPES 2-(4-(2-hydroxyethyl)-1-piperazino)ethanesulfonic acid
Ca: calcium
mM: millimol/liter.

I claim:

1. A method for the determination of Factor XIII in a Factor XIII-containing sample in which the sample is activated with thrombin in the presence of a fibrin-aggregation inhibitor and incubated with a substrate for Factor XIII, with a primary amine and with a buffer substance in solution, and the ammonia which is formed is determined using NADH, glutamic dehydrogenase and ketoglutarate, wherein the substrate for Factor XIII is X-Gly-Pro-Gly-Gln-Ser-Lys-Val-Y-Gly-amide wherein X is selected from the group consisting of H, at least one naturally occurring amino acid, the D-form of at least one naturally occurring amino acid, and a dipeptide formed by any of these amino acids; and
wherein Y is selected from the group consisting of Ile and Leu.

2. The method of claim 1, wherein 2500 IU/l to 20,000 IU/l thrombin are dissolved in a HEPES/sodium chloride buffer which contains 10 mM to 75 mM HEPES and 75 mM to 200 mM NaCl.

3. The method of claim 1, wherein Gly-Pro-Arg-Pro is used as fibrin-aggregation inhibitor.

4. The method of claim 1, wherein 1 mM to 20 mM alphaketoglutarate, 0.05 mM to 0.5 mM NADH and 500 IU/l to 6000 IU/l GLDH are used.

5. The method of claim 1, wherein the amine is chosen from the group consisting of ethanolamine, putrescine, cadaverine, diaminoethane, aminoethane, glycine ethyl and methyl ester.

6. A kit containing means for the detection of factor XIII, containing a fibrin-aggregation inhibitor and a glutamine-containing peptide of claim 1.

7. The method of claim 1, wherein X is selected from the group consisting of Leu-Leu, Arg-Leu, Leu and H-.

8. The method of claim 1, wherein X=Leu.

9. The method of claim 1, wherein said Factor XIII-containing sample is plasma.

10. The method of claim 2, wherein 7000 IU/l of thrombin is used.

11. The method of claim 2, wherein 30 mM of HEPES is used.

12. The method of claim 2, wherein 100 mM of NaCl is used.

* * * * *